United States Patent [19]

Henry et al.

[11] 4,056,535

[45] Nov. 1, 1977

[54] N-SUBSTITUTED 3-AMINOPYRROLIDINES

[75] Inventors: David W. Henry, Menlo Park; Priscilla A. Sturm, Mountain View, both of Calif.

[73] Assignee: Stanford Research Institute, Menlo Park, Calif.

[21] Appl. No.: 679,718

[22] Filed: Apr. 23, 1976

Related U.S. Application Data

[63] Continuation-in-part of Ser. No. 594,511, July 9, 1975, abandoned.

[51] Int. Cl.$^2$ ............................................ C07D 207/14
[52] U.S. Cl. .............................. 260/326.2; 260/326.4; 260/326.85; 424/274
[58] Field of Search ........................... 260/326.2, 326.4

[56] References Cited

U.S. PATENT DOCUMENTS

| | | | |
|---|---|---|---|
| 3,342,826 | 9/1967 | Ruller et al. | 260/326.47 |
| 3,509,171 | 4/1970 | Welstead et al. | 260/326.4 |
| 3,577,440 | 5/1971 | Lunsford et al. | 260/326.85 |

*Primary Examiner*—Paul M. Coughlan, Jr.
*Assistant Examiner*—Mary Vaughn
*Attorney, Agent, or Firm*—Donovan J. De Witt

[57] ABSTRACT

The compounds 3-(N-diethylcarbamyl)amino-1-methyl pyrrolidine, 3-(N-carbethoxy-N-methyl)amino-1-methyl pyrrolidine, 1-diethylcarbamyl-3-(N-methyl-)amino pyrrolidine and 1-diethylcarbamyl-3-dimethylamino pyrrolidine, said compounds having utility as antifilarial agents.

3 Claims, No Drawings

N-SUBSTITUTED 3-AMINOPYRROLIDINES

ORIGIN OF INVENTION

The invention described herein was made in the course of work under a grant or award from the Department of Health, Education and Welfare.

RELATED APPLICATION

This application is a continuation-in-part of Ser. No. 594,511, filed July 9, 1975, now abandoned.

SUMMARY OF THE INVENTION

This invention related to the antifilarial compounds 3-(N-diethylcarbamyl)amino-1-methyl pyrrolidine (I), 3-(N-carbethoxy-N-methyl)amino-1-methyl pyrrolidine (II), 1-diethylcarbamyl-3-(N-methyl)amino pyrrolidine (III) and 1-diethylcarbamyl-3-diemthylamino pyrrolidine (IV), wherein the Roman Numerals I–IV correspond to Examples 1, 2, 3 and 4, respectively, which describe the preparation of the indicated compounds.

Compounds I–IV have the general structural formula:

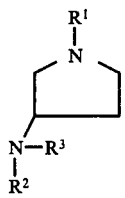

wherein $R^1$ may be $-CH_3$ or $-CON(C_2H_5)_2$ and wherein, when $R^1$ is $-CH_3$, $R^2$ may be $-CON(C_2H_5)_2$ and $R^3$ be $-H$ or $R^2$ may be $-CO_2C_2H_5$ and $R^3$ be $-CH_3$, and wherein, when $R^1$ is $-CON-(C_2H_5)_2$, $R^2$ may be $-CH_3$ and $R^3$ be $-H$ or $-CH_3$. Also included in the invention are pharmaceutically acceptable salts of these compounds, the salts being acid addition salts and water-soluble.

A method of preparing each of the foregoing compounds is presented in the following examples. In general, however, in the 1-methyl pyrrolidine series (compounds I and II) cyclization of 1,4-dibromo-2-butanol to yield 1-methyl-3-pyrrolidinol was followed by chlorination to give 3-chloro-1-methyl pyrrolidine. Substitution with benzylamine provided the nitrogen substituent 3-(N-benzyl)amino-1-methyl pyrrolidine which was acylated with diethylcarbamyl chloride and debenzylated to yield compound I. Methylation of 3-(N-benzyl)amino-1-methyl pyrrolidine gave compound 3-(N-benzyl-N-methyl)-amino-1-methyl pyrrolidine which was debenzylated to 1-methyl-3-(N-methyl)amino pyrrolidine and acylated with ethyl chloroformate to give compound II. Synthesis of the 1-acylated pyrrolidine compounds III and IV commenced by treated commercially available 3-pyrrolidinol with diethylcarbamyl chloride to yield 1-diethylcarbamyl-3-hydroxy pyrrolidine. The 3-benzylamino analog 3-(N-benzyl)amino-1-diethylcarbamyl pyrrolidine was obtained by treatment of 1-diethylcarbamyl-3-hydroxy pyrrolidine with thionyl chloride followed by benzylamine. Subsequent methylation yielded the compound 3-(N-benzyl-N-methyl)amino-1-diethylcarbamyl pyrrolidine which, on debenzylation gave the compound III. Subsequent methylation of III yielded the compound IV.

EXAMPLE 1

3-(N-Diethylcarbamyl)amino-1-methyl pyrrolidine

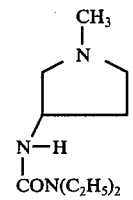

1-Methyl-3-pyrrolidinol (P. S. Portoghese and A. A. Mikhail, J. Org. Chem. 31, 1059 (1966).) This compound was initially prepared according to the literature from 1,4-dibromobutan-2-ol and $CH_3NH_2$ for 25% yield of a colorless liquid, bp 119°–124° at 100 mm Hg (lit. bp 101°–102°/33 mm Hg). On a large scale (300 g dibromobutan-2-ol), however, a highly exothermic reaction occurred on combination of the reactants in an autoclave. Thus, the reaction was repeated by adding the butanol dropwise to the chilled methylamine. EtOH solution in a round bottom flask before placing in the autoclave. After heating in the autoclave, the two portions (a mixture of liquid and solid) were combined; the EtOH was distilled; 1200 ml $H_2O$ was added; and extracted 3 times with $Et_2O$. The aqueous solution was then made very alkaline with 50% NaOH, saturated with $K_2CO_3$, and extracted 2 times with $Et_2O$ plus 2 times with $CHCl_3$. Without drying, the combined extracts were distilled at atmospheric pressure to eliminate solvents (500 ml ). Distillation was continued at 107 mm to yield in four fractions, 115.28 g liquid, boiling range 31°–66°. At this point, solid was present in the distilling flask. Most of the dark amber liquid residue was decanted. The remaining residue was filtered and the solid was rinsed with $CHCl_3$. The filtrate plus the decanted liquid were combined and distilled at atmospheric pressure to remove $CHCl_3$ and then at 90 mm Hg to yield 51.97 g (43%) colorless liquid, bp 115°–120°.

3-Chloro-1-methyl pyrrolidine

A solution of 34.301 g 1 methyl-3-pyrrolidinol (0.340 mol) in 147 ml $CHCl_3$ was chlorinated according to the literature procedure. (J. W. Reinertson and P. E. Thompson, Antibiot. Chemo. 5, 566 (1955).) Acidification with dry HCl must be carefully monitored since the end point was sudden and over-acidification resulted in poor yields. Distillation of the crude product yielded 19.7 g (48.5%) colorless liquid, bp 96°–139° at 760 mm (lit. bp 135°/760 mm).

3-(N-Benzyl)amino-1-methyl pyrrolidine

Compound 3-chloro-1-methyl pyrrolidine, 1.33 g (0.0111 mol), and 6.9 ml (6.3 g, 0.063 mol) benzylamine were combined and gently refluxed at 150° for 8 hr. $Et_2O$ was added to the cooled reaction and the white solid that formed (benzylamine.HCl) was filtered. The filtrate was distilled at atmospheric pressure to remove $Et_2O$, then at water aspirator vacuum to remove benzylamine (bp 78°–85°) and then at 0.1 mm Hg to yield 1.24 g (52%) colorless liquid, bp 85°–88°. This was dissolved in 150 ml $Et_2O$, treated with 2.3 ml 6N ethanolic HCl, stirred in ice for 1 hr, and filtered. Trituration in hot abs. EtOH followed by filtration yielded 0.55 g white solid, mp 105°–110°. An additional 0.1 g crystallized from the mother liquor, mp 113°–118°. A white solid weighting 0.5 g, mp 90°–98°, was precipitated from the mother liquor with Et₂O. The HCl.salt, mp 113°–118°, analyzed as an hydrate. Analysis calculated for C₁₂H₁₈N₂.2HCl.H₂O (percent): C, 51.25; H, 7.89; N, 9.96. Found (percent): C, 51.04; H, 7.61; N, 9.78.

3(N-Diethylcarbamyl)amino-1-methyl pyrrolidine

To a solution of compound 3-(N-benzyl)amino-1-methyl pyrrolidine, 10.0 g (0.053 mol), and triethylamine, 8.1 ml (0.058 mol), in 40 ml dry dioxane was added 7.85 g (0.058 mol) diethylcarbamyl chloride. A voluminous solid was present after 10 min. The reaction was stirred at room temperature for 18 hr. After 2 hr, 15 ml additional dioxane was added to enable resumption of stirring. Et₂O was added to precipitate all triethylamine hydrochloride and the mixture was filtered, rinsing with Et₂O. The filtrate was evaporated to dryness to give a theoretical yield of a yellow oil. A solution of this crude intermediate, 14.7 g (0.051 mol), in 500 ml EtOH and 16 ml 6N ethanolic HCl was hydrogenated at room temperature and atmospheric pressure in the presence of 1.6 g 10% Pd/C for 24 hr. The reaction was filtered and evaporated to dryness. The purplish solid was triturated in acetone. Filtration yielded a white solid, 7.1 g, mp 150°–155°. Analysis calculated for C₁₀H₂₁N₃O.HCl (percent): C, 50.95; H, 9.41; N, 17.82. Found (percent): C, 50.69; H, 9.48; N, 17.81.

EXAMPLE 2

3-(N-Carbethoxy-N-methyl)amino-1-methyl pyrrolidine

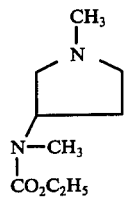

3-(N-Benzyl-N-methyl)amino-1-methyl pyrrolidine

Compound 3-(N-benzyl)amino-1-methyl pyrrolidine was methylated as reported below in Example 3 for preparing the compound 3-(N-benzyl-N-methyl)amino-1-diethylcarbamyl pyrrolidine. A theoretical yield of the crude product was isolated as an oil and characterized as a yellow-orange picrate, mp 215°–220° dec (trituration in hot EtOH). Analysis calculated for C₁₃H₂₀N₂.2C₆H₃N₃O₇ (percent): C, 45.32; H, 3.96; N, 16.91. Found (percent): C, 45.61; H, 3.79; N, 16.86.

1-Methyl-3-(N-methyl)amino pyrrolidine

A solution of 3.08 g compound 3-(N-benzyl-N-methyl)amino-1-methyl pyrrolidine in 150 ml 95% EtOH and 6 ml 6N ethanolic HCl combined with 0.3 g 10% Pd/C was hydrogenated at room temperature and atmospheric pressure for 21 hr. The reaction was filtered and evaporated to a viscous oil which was characterized as a yellow picrate salt, mp 218°–220° dec (trituration in hot EtOH). Analysis calculated for C₆H₁₄N₂.2C₆H₃N₃O₇ (percent): C, 37.77; H, 3.52; N, 19.58. Found (percent): C, 37.99; H, 3.59; N, 19.56.

A reaction run on a larger scale (16.0 g compound 3-(N-benzyl-N-methyl)amino-1-methyl pyrrolidine required addition of fresh 10% Pd/C after 24 hr in order to effect complete hydrogenolysis.

3-(N-Carbethoxy-N-methyl)amino-1-methyl pyrrolidine

Compound 1-methyl-3-(N-methyl)amino pyrrolidine.2HCl, 14.8 g (0.0792 mol) as a gum, was combined with 110 ml dioxane to which it appeared impervious. Upon addition of 45 ml (0.324 mol) triethylamine, a slight cloudiness developed. This combination was stirred in the presence of Linde 3A molecular sieves for 2 hr at room temperature. Then with ice cooling, 11.4 ml (0.119 mol) of ethyl chloroformate was added rapidly from a pipette. Stirring at room temperature was resumed. Within 2-3 hr, much solid was present; stirring was continued for 66 hr. Hot H₂O (200 ml) was added and stirred 1 hr to decompose excess ethyl chloroformate; the creamy-colored opaque (due to disintegrated sieves) solution (pH 7) was extracted 2 times with CHCl₃. NaOH (10%) was then added and the solution again was extracted 2 times with CHCl₃. After drying (Na₂SO₄), filtering, and evaporating the extracts, a total of 7.4 g amber oil was obtained which was distilled twice at 1 mm Hg to yield 1.8 g oil, bp 81.5°–95°. This material was combined with 0.5 g isolated from a previous reaction and redistilled at 0.55-0.65 mm Hg to yield 1.6 g pale yellow oil, bp 73°–77° (9.2%). Analysis calculated for C₉H₁₈N₂O₂ (percent): C, 57.04; N, 9.74; N, 15.04. Found (percent): C, 57.79; H, 9.75; N, 14.83.

EXAMPLE 3

1-Diethylcarbamyl-3-(N-methyl)amino pyrrolidine

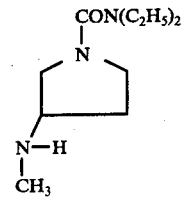

1-Diethylcarbamyl-3-hydroxy pyrrolidine

To a cold (0°) stirring two phase system of 28.9 g (0.332 mol) 3-pyrrolidinol in 250 ml Et₂O and 17.4 g NaOH in 217 ml H₂O was added 53.8 g (0.397 mol) of diethylcarbamyl chloride dropwise rapidly over approximately 15 min. The ice bath was removed and Et₂O was seen refluxing 20 min later. The reaction flask was fitted with a condenser and stirred 18 hr (refluxing last 10 min). The two phases were separated; the Et₂O layer was dried (Na₂SO₄), filtered and evaporated to yield 8.3 g amber oil. The water layer, after extraction with CHCl₃, yielded an additional 29.7 g amber oil. Distillation of the combined oils at 0.2 mm Hg gave three fractions with 1-diethylcarbamyl-3-hydroxy pyrrolidine (18.5 g, 30%) collected at bp 120°–130°.

An analytical sample was isolated from a previous reaction, bp 100°–120° at 0.075 mm Hg. Analysis calculated for C₉H₁₈N₂O₂.½H₂O (percent): C, 55,36; H, 9.81; N, 14.35. Found (percent): C, 55.71; H, 9.60; N, 14.30.

3-(N-Benzyl)amino-1-diethylcarbamyl pyrrolidine

A solution of 1-diethylcarbamyl-3-hydroxy pyrrolidine, 21.0 g (0.113 mol), in CHCl₃ (84 ml) was brought to pH 1 by treatment with dry HCl. SOCl₂, 9.0 ml (0.124 mol), was rapidly added dropwise with vigorous stirring at room temperature. Heat and gas were produced. After addition was completed, the reaction was heated at reflux and monitored by thin-layer chromatography (EtOAc) at 1, 1.5 and 2 hr. No progress was seen after 1 hr. At 2 hr an additional 1 ml $SOCl_2$ was added, after 0.5 hr, a spot additional to that of product and starting material was seen. The reaction was cooled, poured on ice, made alkaline with solid $NaHCO_3$, and the $CHCl_3$ and $H_2O$ layers were separated. The $CHCl_3$ layer was washed once with $H_2O$, dried $(Na_2SO_4)$, filtered and evaporated to dryness to yield 25.94 g (100% +) dark viscous oil which was distilled through a Vigreaux head at 0.1 mm Hg to yield 4 fractions, the product (15.4 g, 67%) distilling at 80°–84°.

This intermediate, 13.96 g (0.068 mol), was refluxed at 160° with 37.4 ml benzylamine (0.342 mol) for 8 hr. $H_2O$, 200 ml, was added to the pale apricot-colored mixture of liquid and white solid; the solid dissolved and an oil separated. This was extracted 3 times with $Et_2O$ and combined extracts were washed with 50 ml $H_2O$, dried $(Na_2SO_4)$, filtered, and evaporated i.v. to yield 23.43 g (benzylamine present) yellow oil. This was chromatographed on a 3136 g alumina (Woelm) dry column (B. Loev and M. M. Goodman, Chem. Indus. 2026 (1967).) developed with $CHCl_3$. Several fractions were cut and eluted with EtOAc. In this way 9.3 g (49%) still impure product was obtained. This was used directly in the next reaction. A picrate of 3-(N-benzyl-)amino-1-diethylcarbamyl pyrrolidine was isolated from an initial probe, mp 71°–76° after recryst from 50% aq. EtOH. Analysis calculated for $C_{16}H_{25}N_3O.C_6H_3N_3O_7.H_2O$ (percent): C, 50.57; H, 5.79; N, 16.08. Found (percent): C, 51.00; H, 5.65; N, 16.13.

3-(N-Benzyl-N-methyl)amino-1-diethylcarbamyl pyrrolidine

To a stirring solution of 0.275 g (0.001 mol) compound 3-(N-benzyl)amino-1-diethylcarbamyl pyrrolidine in 3 ml $CH_3CN$ was added 0.4 ml 37% aq. HCHO (0.005 mol) followed by 0.100 g $NaBH_3CN$ (hygroscopic). The reaction was stirred 1.5 hr, HOAc added to bring to neutrality and stirred an additional 1 hr. The reaction was evaporated to dryness, 10 ml 10% aq. NaOH added, extracted 3 times with $Et_2O$, dried $(Na_2SO_4)$, filtered, and again evaporated to dryness to give 224 mg (78%) yellow oil which was homogeneous on tlc. A solution of 3-(N-benzyl-N-methyl)amino-1-diethylcarbamyl pyrrolidine in 50 ml $Et_2O$, was treated with a saturated solution of maleic acid in EtOH until no increase in cloudiness was seen. Stirring in ice produced a white crystalline solid. Filtration yielded 0.192 g (47.5%) 1-diethylcarbamyl-3-dimethylamino pyrrolidine $.C_4H_4O_4$, mp 117°–119°. Analysis calculated for $C_{17}H_{27}N_3 O.C_4H_4O_4$ (percent): C, 62.20; H, 7.71; N, 10.36. Found (percent): C, 62.16; H, 7.71; N, 10.21.

1-Diethylcarbamyl-3-(N-methyl)amino pyrrolidine

A solution of compound 3-(N-benzyl-N-methyl)amino-1-diethylcarbamyl pyrrolidine.$C_4H_4O_4$, 7.0 g (0.0173 mol), in aq. MeOH (approximately 100 ml of 90%) was converted to the hydrochloride by stirring with 70 g Dowex X-4 (Cl$^-$ form) ion exchange resin (mesh 20–50) overnight and filtering, rinsing the resin twice with MeOH. Evaporation of the filtrate to dryness gave 5.35 g (0.0164 mol) of the hydrochloride as an oil. A solution of this in 250 ml 95% EtOH was combined with 0.5 g 10% Pd/C and stirred under $H_2$ at room temperature in a burette. Hydrogenation was complete in 1 hr. The reaction was filtered and evaporated to dryness. The oil was dissolved in a minimum amount of abs. EtOH and treated with 1.5 liters of dry $Et_2O$. A very hygroscopic HCl salt was isolated. Therefore the $Et_2O.EtOH$ was evaporated; the residue treated with 10% NaOH, saturated with $K_2CO_3$, and extracted 3 times with $CHCl_3$. The combined extracts were dried $(Na_2SO_4)$, filtered and evaporated to yield 3.073 g (94%) oil. An ethereal solution of a portion of the free base (1.248 g) was treated with 0.727 g maleic acid, dissolved in a minimum amount of EtOH, to yield 1.5 g white solid, mp 98°–100°. Analysis calculated for $C_{10}H_{21}N_3O.C_4H_4O_4$ (percent): C, 53.32; H, 7.99; N, 13.32. Found (percent): C, 53.54; H, 7.88; N, 13.52. A picrate, mp 152.5°–153°, was isolated from a previous reaction. Analysis calculated for $C_{10}H_{21}N_3O.C_6G_3N_3O_7$ (percent): C, 44.86; H, 5.65; N, 19.62. Found (percent): C, 44.88; H, 5.58; N, 19.59.

EXAMPLE 4

1-Diethylcarbamyl-3-dimethylamino pyrrolidine

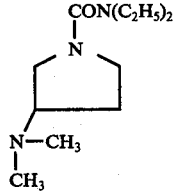

1-Diethylcarbamyl-3-dimethylamino pyrrolidine

Compound 1-diethylcarbamyl-3-(N-methyl)amino pyrrolidine, 0.308 g (0.00155 mol) was methylated as previously described for 3-(N-benzyl-N-methyl)amino-1-diethylcarbamyl pyrrolidine. An oil (0.284 g, 86%), homogeneous on tlc, was isolated. A solution of the oil in 50 ml $Et_2O$ was treated with 154 mg maleic acid dissolved in a minimum volume of EtOH to yield 0.280 g (55%) shiny plates, mp 121°–123°. Analysis calculated for $C_{11}H_{23}N_3O.C_4H_4O_4$ (percent): C, 54.70; H, 8.26; N, 12.76. Found (percent): C, 54,66; H, 8.30; N, 12.74.

The compounds of the present invention are effective as antifilarial agents. Diseases involving filariasis of one type or another are of wide-spread occurrence in tropical areas throughout the world. Proposed antifilarial agents of potential use in combating these diseases can be screened by administering the active compounds to rodents having relatively high blood microfilaria levels. The efficacy of the compounds is then determined by observing the change in said levels occasioned by administration of the drugs. The latter is effected using aqueous solutions of the test compounds, as administered by gavage. Table I, to follow, presents the biological results obtained in such a study using each of the four compounds of the present invention. In each case the procedure entailed an increasing daily dosage schedule in which drugs were administered to birds previously infected with *Litomosoides carinii* at dosages of 25, 50, 100 and 200 mg/kg of body weight, on days 0, 1, 2 and 3 of the test procedure. Blood microfilaria levels were determined before treatment and on days 1, 3, 7, 9 and 14 of the experiment. Due to its relatively short duration, this dosage program was ineffective to kill adult worms present in the animal. However, as will be seen from the Table, each of the compounds afforded a large decrease in the blood microfilaria count even after one day of the treatment. The details of the antifilaria evaluation procedure are presented in the publication of Priscilla A. Sturm and David W. Henry entitled "Antifilarial Agents. Diazabicyclooctanes and Diazabicycloheptanes as Bridged Analogs of Diethylcarbamazine," Journal of Medicinal Chemistry, Vol. 17, No. 5, pp. 481–487, (1974). The disclosures of the publication are specifically incorporated herein by reference.

The compounds of the present invention have been described in the examples in the form of acid addition salts, such salts being water soluble and therefore of somewhat greater utility than the compounds would be without the inclusion of the acid component. In preparing the compounds as salts, any pharmaceutically acceptable acid material may be employed, e.g. hydrochloride acid, sulfuric acid, citric acid, or acetic acid, for example. The pure compounds can be prepared in non-salt form by treating the salt with alkali in aqueous solution, the compound being extracted from the aqueous reaction system with a solvent such as diethyl ether or chloroform. The evaporation of the solvent then leaves the compound, usually in form of an oil.

TABLE I

Antifilarial Properties of Examples 1–4 Compounds

| Compound | mp(° C) | Microfilaria Count, Day 0 (range) | Antifilarial Activity[a] % of Day 0 Count (Std. dev.) | | | | |
|---|---|---|---|---|---|---|---|
| | | | Day 1 | Day 3 | Day 7 | Day 9 | Day 14 or 15 |
| Ex 1 | 150–155° C | 270(131–494) | 67(±10) | 7(±5) | 14(±4) | | 51(±18) |
| Ex 2 | [b] | 277(113–471) | 85(±18) | 11(±6) | 18(±3) | | 80(±26) |
| Ex 3 | 98–100° C | 195(132–322) | 105(±21) | 39(±15) | 46(±25) | | 99(±31) |
| Ex 4 | 121–123° C | 424(183–676) | 31(±19) | 2(±2) | 11(±7) | | 62(±31) |

[a]Drugs administered at dosages of 25, 50, 100, and 200 mg/kg on days 0, 1, 2, 3, respectively.
[b]Boiling point 73–77° at 0.55–0.65 mm.

What is claimed is:

1. The compounds having the structure

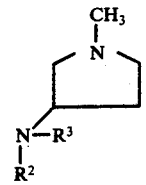

wherein $R^2$ may be $-CON(C_2H_5)_2$ and $R^3$ be $-H$, or $R^2$ may be $-CO_2C_2H_5$ and $R^3$ be $-CH_3$, and the pharmaceutically acceptable acid addition salts thereof.

2. The compound of claim 1 which is 3-(N-diethylcarbamyl)amino-1-methyl pyrrolidine, or the pharmaceutically acceptable acid addition salts thereof.

3. The compound of claim 1 which is 3-(N-carbethoxy-N-methyl)amino-1-methyl pyrrolidine, or the pharmaceutically acceptable acid addition salts thereof.

* * * * *